(12) United States Patent
Bauss

(10) Patent No.: US 11,744,953 B2
(45) Date of Patent: Sep. 5, 2023

(54) DEVICE AND SYSTEM FOR OBTAINING MEDICAMENT RELATED INFORMATION

(71) Applicant: Carebay Europe Ltd., Sliema (MT)

(72) Inventor: Markus Bauss, Lengdorf (DE)

(73) Assignee: SHL MEDICAL AG, Zug (CH)

(*) Notice: Subject to any disclaimer, the term of this patent is extended or adjusted under 35 U.S.C. 154(b) by 445 days.

(21) Appl. No.: 16/319,706

(22) PCT Filed: Jun. 28, 2017

(86) PCT No.: PCT/EP2017/065947
§ 371 (c)(1),
(2) Date: Jan. 22, 2019

(87) PCT Pub. No.: WO2018/015118
PCT Pub. Date: Jan. 25, 2018

(65) Prior Publication Data
US 2021/0275754 A1    Sep. 9, 2021

(30) Foreign Application Priority Data

Jul. 22, 2016    (EP) .................................... 16180921

(51) Int. Cl.
| A61M 5/00 | (2006.01) |
| A61M 5/315 | (2006.01) |
| G06K 19/06 | (2006.01) |
| G16H 20/10 | (2018.01) |

(52) U.S. Cl.
CPC ........ *A61M 5/31568* (2013.01); *A61M 5/002* (2013.01); *G06K 19/06028* (2013.01);
(Continued)

(58) Field of Classification Search
CPC .............. A61M 5/31568; A61M 5/002; A61M 2205/3561; A61M 2205/3584;
(Continued)

(56) References Cited

U.S. PATENT DOCUMENTS

| 3,021,245 A | 2/1962 | Roberts et al. |
| 2006/0067713 A1 | 3/2006 | Farooqui et al. |

(Continued)

FOREIGN PATENT DOCUMENTS

| JP | H11-276583 A | 10/1999 |
| JP | 2010-29673 A | 2/2010 |
| WO | 2016055401 A1 | 4/2016 |

OTHER PUBLICATIONS

English Translation of Abstract of Japanese Patent Application No. H11-276583 dated Jan. 18, 2019.

(Continued)

*Primary Examiner* — Lauren P Farrar
*Assistant Examiner* — Hamza A Darb
(74) *Attorney, Agent, or Firm* — MCDONNELL BOEHNEN HULBERT & BERGHOFF LLP

(57) ABSTRACT

The present invention relates to a system for obtaining medicament related information of specific medicaments, the in system comprising a device (10, 50) for obtaining medicament related information, the device comprising a recording unit, said recording unit comprising a reader (20, 32; 86, 88, 92, 122), capable of reading information pertained to specific medicaments, said recording unit further comprising a memory module (22, 104) capable of storing information read by said reader (20, 32; 86, 88, 92, 122), wherein said reader (20, 32; 86, 88, 92, 122) is arranged with a three-dimensional contact interface (81) designed to interact with a corresponding contact surface (87) containing information related to specific medicaments.

17 Claims, 4 Drawing Sheets

(52) U.S. Cl.
CPC ....... *G06K 19/06037* (2013.01); *G16H 20/10* (2018.01); *A61M 2205/3561* (2013.01); *A61M 2205/3584* (2013.01); *A61M 2205/3592* (2013.01); *A61M 2205/52* (2013.01); *A61M 2205/6072* (2013.01)

(58) Field of Classification Search
CPC ...... A61M 2205/3592; A61M 2205/52; A61M 2205/6072; A61M 2205/35; A61M 2205/3576; A61M 2205/6036; A61M 2205/6045; A61M 5/24; A61M 5/008; G06K 19/06028; G06K 19/06037; G16H 20/10; G16H 20/13; G16H 40/63
See application file for complete search history.

(56) References Cited

U.S. PATENT DOCUMENTS

| | | | |
|---|---|---|---|
| 2009/0258678 A1 | 10/2009 | Chava et al. | |
| 2013/0204227 A1* | 8/2013 | Bochenko | A61M 39/02 |
| | | | 604/189 |
| 2016/0119753 A1 | 4/2016 | Ostrander et al. | |
| 2016/0206806 A1* | 7/2016 | Wright | A61M 5/3158 |

OTHER PUBLICATIONS

English Translation of Abstract of Japanese Patent Application No. 2010-029673 dated Jan. 18, 2019.
Search Report issued in Taiwanese Patent Application No. 106122574 dated Oct. 18, 2018.

\* cited by examiner

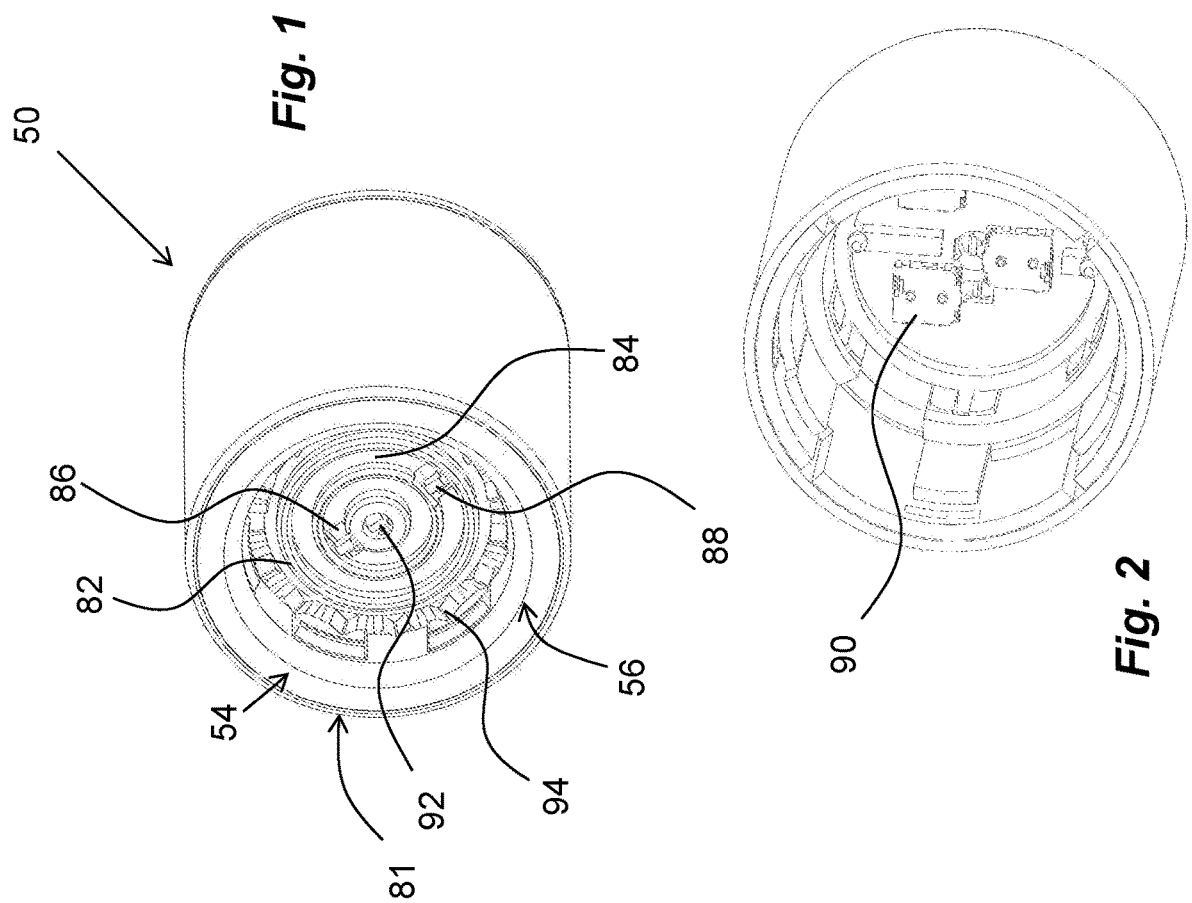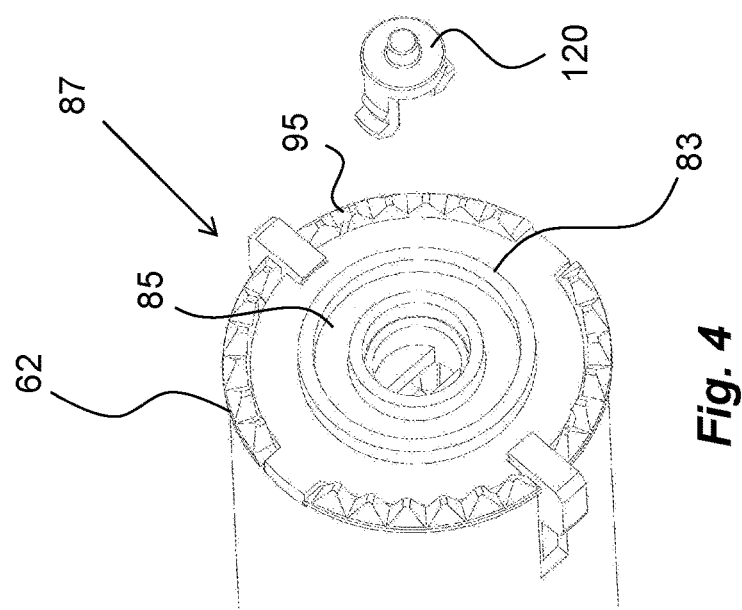

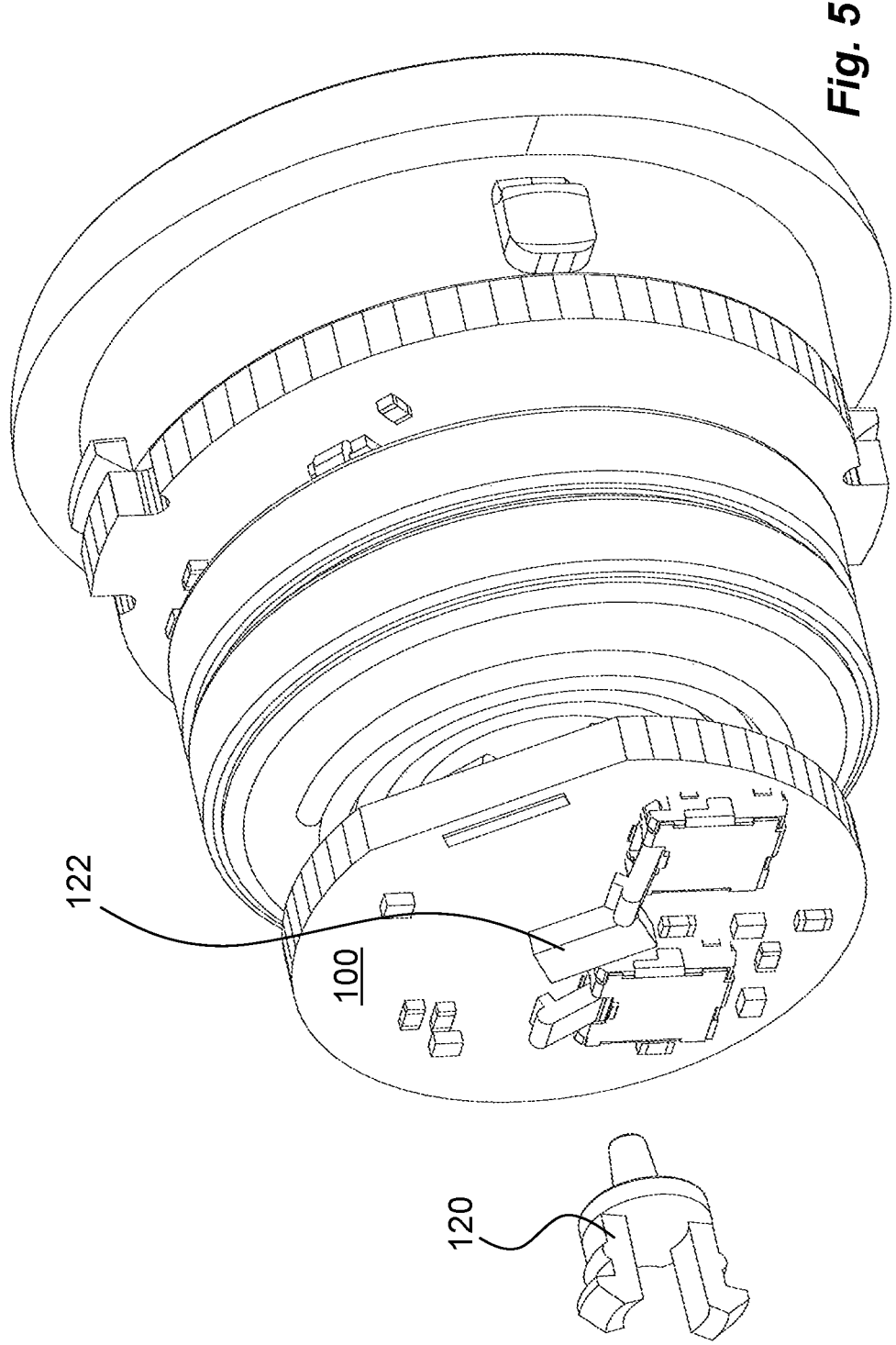

DEVICE AND SYSTEM FOR OBTAINING MEDICAMENT RELATED INFORMATION

CROSS REFERENCE TO RELATED APPLICATIONS

The present application is a U.S. National Phase Application pursuant to 35 U.S.C. § 371 of International Application No. PCT/EP2017/065947 filed Jun. 28, 2017, which claims priority to European Patent Application No. 16180921.5 filed Jul. 22, 2016. The entire disclosure contents of these applications are hereby incorporated by reference into the present application.

TECHNICAL AREA

The present invention relates to a device and a system for obtaining medicament related information and in particular a device and system to be used with medicament delivery devices for personal use.

BACKGROUND OF INVENTION

In many instances there is a treatment scheme that is to be handled by the patient or user himself. Since many of these patients are not very used to handle medicament delivery devices and medicaments and often need help. Especially detecting the type of medicament may be important for an inexperienced user before it is administered. Other information might be the strength of the medicament and also which market the medicament was intended for.

It might also be important to obtain further information regarding the medicament such as when it was manufactured, if and when there is an expiry date, after which the drug should not be used any more. The further information might also be manufacturing batch number or even unit specific identification.

BRIEF DESCRIPTION OF INVENTION

The aim of the present invention is to provide a device and a system for obtaining medicament related information of specific medicaments in an easy way, which information may be stored and handled for further use.

The aim is obtained by a system according to the features of the independent patent claim. Preferable embodiments of the invention form the subject of the dependent patent claims.

According to a main aspect of the invention, it comprises a system for tracking specific medicaments, wherein the system may comprise a device for obtaining medicament related information, hereafter named tracker, which tracker may comprise a reader capable of reading information pertained to specific medicaments. The recording unit may further comprise a memory module capable of storing information read by said reader.

According to one aspect, the reader of the tracker may be arranged with a three-dimensional contact surface designed to interact with a corresponding contact surface of the system, containing information related to specific medicaments. In this regard, the three-dimensional contact surface of the reader may be arranged with activation elements that engage with the corresponding contact surface containing information related to the medicaments. The three-dimensional contact surfaces may be placed on or embossed in packaging material that the medicament is delivered in. This may for example be done in e.g. a plastic holding tray that a syringe for a medicament delivery device is delivered in. The three-dimensional contact surface is then formed at the same time as the tray is formed for holding the medicament container. On the other hand, the tree-dimensional contact surface could be produced on a label that is attached to a primary or secondary package of a specific medicament. The three-dimensional contact surface may be customized so that only specific trackers can be in contact with and read the data provided from the contact surface.

According to one feasible solution, the tracker is arranged with a number of switches that are activated when the tracker is connected to the contact surface. If more than one switch is present, they may be operated differently, i.e. on or off, depending on the information to be provided. In this regard, the more switches, the larger number of combinations are possible and thus the more information may be obtained.

Further, in addition to the three-dimensional contact surfaces, there may be provided additional information contained in one-dimensional or two-dimensional printed elements, such as bar codes, alpha numerical codes, QR-codes or micro dot patterns. The tracker may then in addition be arranged with suitable reading elements that can derive information from the printed elements. As an alternative, the additional information may be contained in an RFID or NFC chip, wherein the tracker is arranged with a reader that can derive information from the chip. It is also feasible that the additional information is arranged on an element that is exchangeable on the contact surface.

In order to present the information obtained by the tracker, it may advantageously comprise user communication elements capable of providing a user with information read by the reader, and according to one aspect, the user communication elements may comprise audio and/or video interfaces. The tracker is then capable of providing information directly to a user. The information could then be presented on a display that could contain text information. As an alternative, the tracker could use a synthetic voice function that can provide the information audibly. Other types of audio/visual information elements may comprise lamps of different colours, with blinking features etc.

The system may in addition be arranged such that the user communication elements comprise transferring elements to external objects. This enables the obtained information to be extracted and used for further handling. This could either be a complement to audio/visual information elements, or they may be omitted and the information be presented by external objects.

According to one feasible solution, the transferring elements may comprise data ports for wired connection with external objects. The tracker could then be wired to e.g. a computer, a smart device or the like and the information stored in the tracker could be transferred via a cable connected to the data port.

As an alternative to wired transfer, the transferring elements may comprise wireless data communication elements. In this case no data cables are necessary. According to one solution, the wireless data communication elements may comprise near frequency communication technology. As an alternative, the data communication elements may comprise cellular radio communication technology. As yet an alternative, the data communication elements may comprise wireless local area networks.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIGS. 1-3 show a variant of a tracker connectable to information contact surfaces, FIG. 4 shows one example of an information contact surface, FIG. 5 shows interaction between a tracker and an activator element.

DETAILED DESCRIPTION OF THE INVENTION

Figure 3:
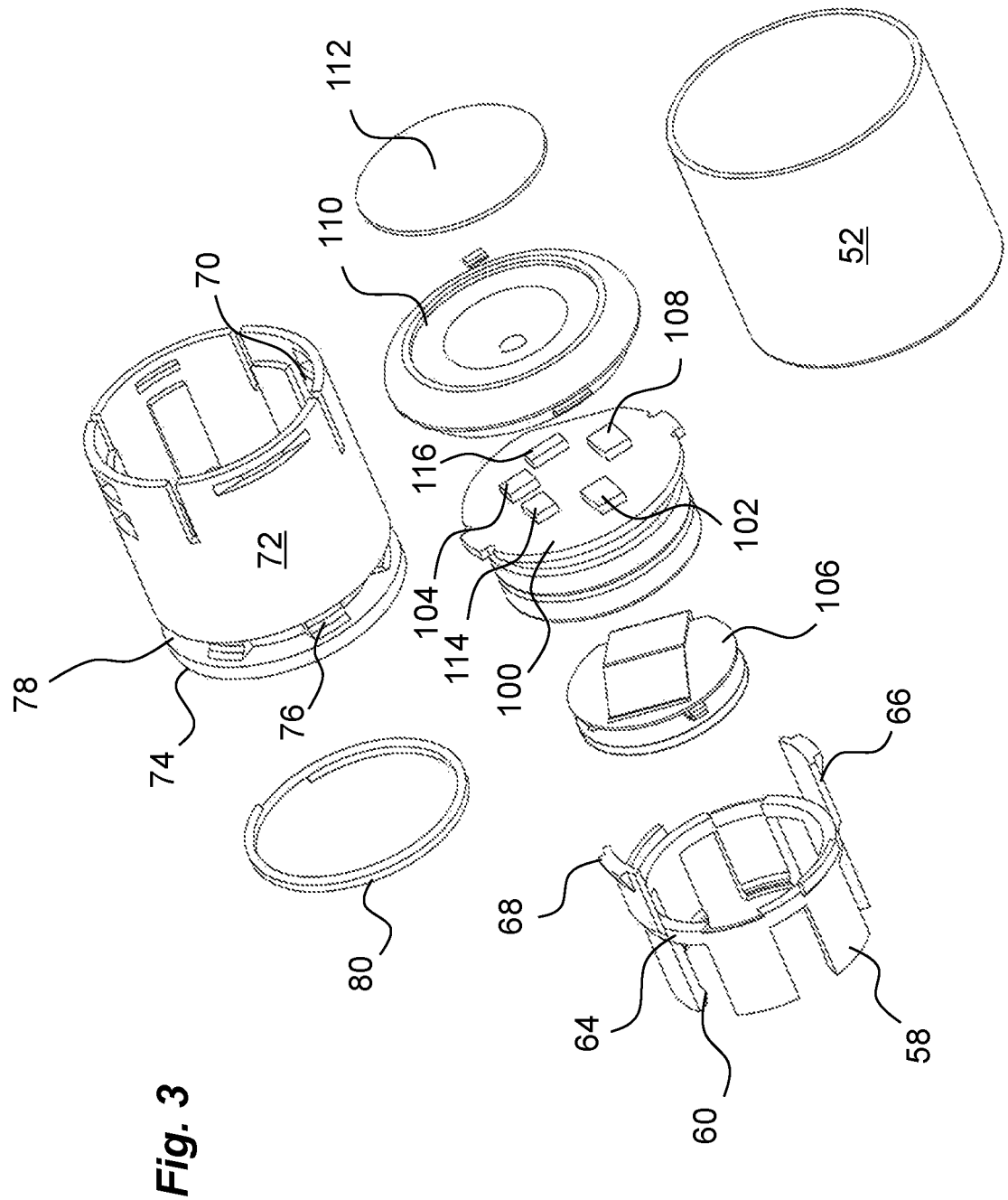
Figure 6C:
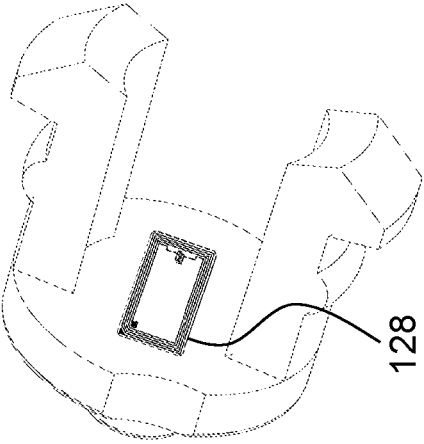
FIGS. 6a-c show activator elements containing different information carriers.
Figure 6B:
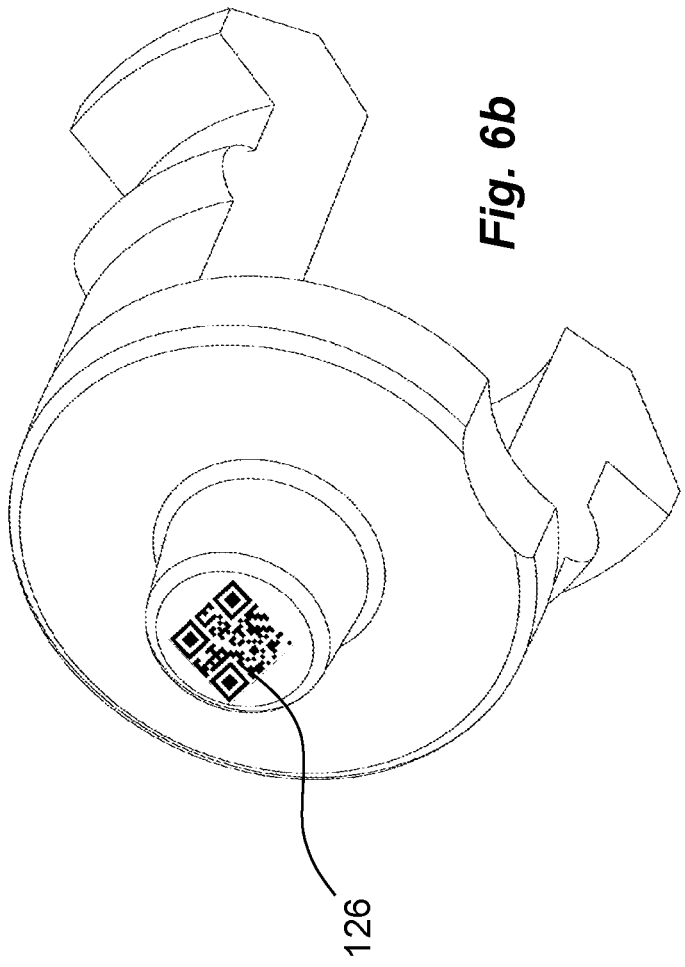
Figure 6A:
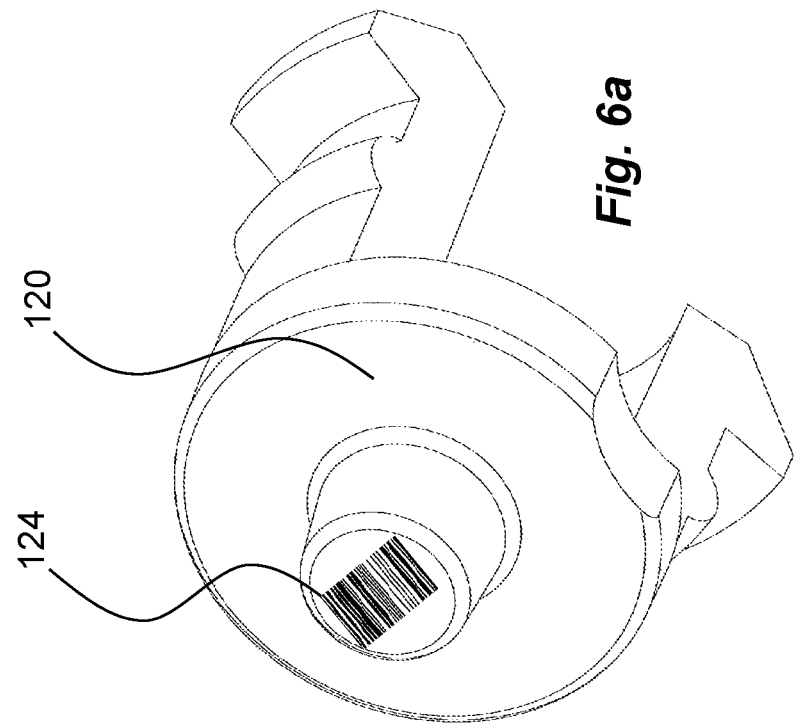

The invention comprises a system that is capable of receiving information regarding specific medicaments. FIGS. 1-3 show a non-limiting embodiment of a tracker 50 that may be used for tracking specific medicaments. The tracker 50 comprises a housing 52 that might have a corresponding shape and appearance as a medicament delivery device. This might be the case if the tracker 50 is arranged to be connected to a medicament delivery device for the purpose of monitoring the use of the medicament delivery device. It is however understood that the connectivity with a medicament delivery device is no prerequisite for the invention.

If however the tracker 50 is to be connectable, either to a medicament delivery device or to some other device, the housing 52 may have a proximally directed attachment mechanism 54 that is designed to interact with a connection surface of a device. In the embodiment shown, the attachment mechanism 54 comprises a central passage 56 which has a shape and dimension so as to fit onto the connection surface.

In order for the connection to be releasable, the attachment mechanism 54 of the tracker 50 comprises locking elements in the form of a number of attachment tongues 58 that are flexible in the generally radial direction. The free ends of the attachment tongues 58 are arranged with inwardly directed ledges 60 that may be designed to cooperate with corresponding locking elements in the form of an annular ledge 62 at the distal end of the housing of the medicament delivery device if such is used. The attachment tongues 58 are attached to a ring-shaped element 64, which ring-shaped element 64 is arranged with two oppositely positioned, distally directed, tongues 66. The free ends of the tongues 66 are arranged with outwardly directed ledges 68, which ledges are arranged to fit into recesses 70 in a tubular holding member 72.

The holding member 72 is arranged with a plate-shaped contact element 74 at its proximal end, where the holding member 72 and the contact element 74 are interconnected by a number of bridges 76. The bridges 76 are placed somewhat radially inwards in relation to the holding member 72 such that an annular recess 78 is formed. Further, in the spaces between the bridges 76 the free ends of the attachment tongues 58 are placed. The attachment tongues 58 and the bridges 76 are designed and positioned such that the outer surfaces of the tongues 58 are placed somewhat radially outside the bridges 76. Further a wire spring 80 is arranged in the annular recess 78, whereby it is in contact with the outer surface of the attachment tongues 58, providing a resilient force in the outwards radial direction.

The tracker 50 may further be arranged with a mechanical interface 81. The mechanical interface may comprise a number of rings 82 and grooves 84 on the proximally directed surface of the contact element 74 having a design that fits together with rings 83 and grooves 85, FIG. 4, of a contact surface 87 that the tracker 50 is to be connected to, forming a contact interface. Further, the contact element 74 is preferably arranged with a number of passages 86, in which passages 86 switches 88 are placed. The switches 88 are operably connected to electrical switching elements 90, FIG. 2, that will enable activation of the monitoring unit as will be described. Preferably the switches 88 are arranged and designed to interact with the contact surface 87 such that the switches 88 are activated when the tracker 50 is attached. Preferably the positions of the switches 88 of the electrical switching elements are arranged in a certain pattern that can be specific for a certain tracker and wherein a certain contact surface 87 has the same design so that a certain number of the switches 88 are activated when the tracker is attached according to a specific pre-arranged specification, where activation of specific switches correlate to specific information regarding the medicament.

For example the contact surfaces are the rings and grooves wherein the switches 88 are positioned at different distances in a radial direction as seen in FIG. 1. The advantage with having rings is that the angular position between the tracker and the contact surface is not important when the two are interconnected. Further, as seen in FIG. 1, since the switches 88 are placed in the grooves 84, manipulation of the switches 88 by fingers is difficult, providing increased security against improper use of the tracker 50.

Further, in order to automatically activate the tracker 50 at the point of contact with a contact surface, the tracker 50 may be provided with an activation switch 92. In the embodiment shown in FIG. 1, this activation switch 92 may be placed in a central position of the interface of the tracker 50.

The interface between the contact surface and the tracker 50 could further comprise mechanical patterns that are to interact with each other. For instance the proximal surface of the contact element 74 could comprise a number of teeth 94 for example around a circumference. These teeth 94 are arranged to cooperate with corresponding teeth 95 on a contact surface, FIG. 4, wherein the number of teeth, the design of the teeth and the positions of the teeth are chosen such that a keying function is obtained. Thus, only trackers and contact surfaces that have the same pattern can be inter-connected. This provides the possibility of customizing the tracker 50 such that only certain connections are possible.

According to one preferable solution, the contact surfaces are arranged on packages of medicament, wherein the packages could be primary packages or secondary packages. Because of the keying function between the tracker and the contact surfaces, a customization could be obtained. For example a tracker may only be connectable to specific packages containing specific medicament. For example, if a patient has been prescribed a certain medicament, he or she is also provided with a tracker that can only be connected to that type of medicament. In this way the risk is reduced that the patient takes the wrong medicament. The level of customization could be from specific medicaments having specific strength to a whole range of medicaments from e.g. the same manufacturer. Further, since there are a number of switches, different information could be obtained by different combinations of activation of the switches being on or off. For example, three switches gives eight combinations and four switches gives 16 combinations, thus providing possibilities of creating data to be obtained by the tracker.

The tracker shown in the drawings may further comprise an electronic circuit 100 comprising a processor 102, FIG. 3, capable of processing data program code for performing different tasks. The data program code is preferably stored in appropriate memory modules 104, in which also retrieved data may be stored, as will be described. The electronic circuit 100 is further arranged with some power supply 106 such as button cells, photovoltaic panels, etc. Further, the above mentioned switching elements 90, 92 are electronically connected to the electronic circuit 100. In this respect it might be that all switches need to be operated at the same time in order for the tracker 50 to be activated. The electronics circuit 100 may further be arranged with user communication elements 108 that is arranged and programmed to communicate with a user. The user communication elements 108 may comprise display elements that can communicate visually, e.g. by text stored in the electronics module that is displayed on a suitable display 110 on the monitoring unit. The display may be protected by a suitable transparent cover or glass 112. In addition to, or instead, the user communication circuit may comprise audio elements 114 that can communicate audibly, e.g. by a recorded message stored in the electronics module that is played in an appropriate loudspeaker of the electronics module or of the device as such.

A further development of the activation function is to provide the tracker 50 with at least one communication circuit 116 comprised in the user communication elements. The communication technologies that the communication circuit 116 may utilize may comprise near range communication technology such as RFID, NFC or the like, as well as Bluetooth, Ant, ZigBee, just to mention a few. This type of wireless communication technology may also be used to activate the monitoring unit. The communication circuit may be used for monitoring the usage of the medicament delivery device such that information is transmitted from the medicament delivery device to the monitoring unit.

According to a possible feature, if the tracker 50 is provided with communication circuits, then monitored data obtained by the monitoring unit may be transferred to external storage sources and/or external devices. If for instance NFC technology is used, then a mobile NFC-enabled device may derive the monitored data from the tracker 50. The same functionality may also be provided when using Bluetooth communication technologies.

The mobile device may then either be capable of processing the data obtained by the tracker or may in turn transmit the monitored data to external databases via the communication technologies of the mobile device, such as cellular radio communication networks, e.g. GSM, 3G, 4G, etc. and/or wireless local area networks, which networks can provide access to the internet and thus to a large number of external data storage sources, data handling centres, etc.

Regarding communication technologies, it is of course possible to incorporate the above mentioned communication technologies in the tracker 50 as such. Then the tracker may communicate directly with external data storage sources, data handling centres etc. via the communication networks.

The contact surface could be arranged with a number of information carrying elements as described above, not only mechanical. One solution in relation with the tracker according to the solution shown in FIGS. 1-6 is to utilize an activator element 120 that is attached to the contact surface. With this solution, the activator element 120 may be customized to contain specific information regarding a certain medicament and may be added to a standard contact surface. For example, the activation element may contain a bar-code with certain information. The tracker is then arranged with reading element 122 that can be a bar code reader that is positioned adjacent the activator element 120. The activator element is arranged with a bar code 124, FIG. 6*a*, on a distally directed surface thereof such that is readable by the bar code reader. As an alternative to the bar code, a QR-code 126, FIG. 6*b*, could be utilized at the distal end of the activator element 120, where the reading element 122 is a QR-code reader. Both the bar code 124 and the QR-code 126 could contain more information that could be obtained by the tracker 50. Another solution could comprise an RFID chip 128, FIG. 6*c*, attached to or molded into the activator element. The reading element 122 of the tracker 50 may then be an RFID reader placed in the vicinity of the activator element, wherein the RFID reader is capable of obtaining data stored in the RFID chip 128. The RFID chip 128 could contain different information that the tracker 50 could derive.

Regarding information that can be obtained by the tracker, there are different "levels" or amount of information that can be available. In a basic version the information could contain a code that just identifies the specific medicament, for example by encoding a numeric or alphanumeric sequence that is unique to a specific medicament. Further information in that respect could then be format of the specific medicament (liquid, tablet, powder) as well as the strength of the specific medicament. Further information may pertain to a specific dedicated country/market/region. This may be used for checking specific medicaments in order to stop possible parallel import issues. The above type of information is specific for products and is the same on all products, sort of fixed information.

Other types of information that can be obtained are more variable. Typical variable information may be batch or unit specific manufacturing data, for example Lot Number and expiration date that difference for each manufacturing batch. In this regard, it is of course possible to include individual numbering or identification for each item so that each item can be tracked individually.

Regarding handling of the information, there might be different "levels" of communication of the information obtained by the tracker. In a simple case, the tracker merely displays the data retrieved to a user when reading it, without any further measures or steps being taken. The next step may be that the tracker will alert a user to take action depending on the information. For example, if the data is variable, the tracker may alert a user if the medicament has expired by comparing with its internal timer function. If the tracker can obtain a country indication, it might instruct a user to check the correctness and possibly alert authorities if there are deficiencies regarding country of sale for instance.

It is to be understood that the invention described above and disclosed in the drawings is to be regarded only as a non-limiting example and that it is defined by the scope of the patent claims.

The invention claimed is:

1. A system for obtaining medicament related information of specific medicaments, the system comprises:
   a first device configured as a medicament delivery device contained within a housing having a terminal distal end, where the first device delivers a medicament contained in the first device directly to a user from a proximal end of the housing that is opposite the terminal distal end, where the terminal distal end comprises an activator projecting distally outward and a distally facing three-dimensional contact surface comprising distally projecting rings or grooves arranged in a first pattern, where the activator contains medicament related information specific to the medicament;

a second device configured with a corresponding shape of the first device and configured for releasable connection to the terminal distal end of the first device so as to monitor usage of medicament by the first device and to transfer usage information from the first device to the second device, where the second device comprises a terminal proximal end comprising a proximally facing three-dimensional contact surface having proximally projecting rings or grooves arranged in a second pattern, where when the first pattern matches and corresponds to the second pattern a connection is possible between the first and second devices to create a contact interface that causes a transfer of the medicament related information from the activator to the second device, the second device comprising:

a recording unit, said recording unit comprising a reader, capable of reading information pertaining to specific medicaments, said recording unit further comprising a memory module capable of storing information read by said reader, wherein the medicament does not transfer from the first device to the second device, wherein the proximally facing three-dimensional contact surface is arranged with one or more proximally facing switches that are activated by contact with one or more distally projecting surfaces on the distally facing three-dimensional contact surface when the contact interface is formed, and wherein the medicament related information contained on the activator is read by the reader when the contact interface is formed.

2. The system according to claim 1, wherein the activator is removably connected to the distally facing three-dimensional contact surface such that the activator is inter-changeable.

3. The system according to claim 1, wherein said information is presented as a bar code.

4. The system according to claim 1, wherein said information is presented as a QR code.

5. The system according to claim 1, wherein said information is presented as a micro-dot pattern.

6. The system according to claim 1, wherein said information is presented as an alphanumeric code.

7. The system according to claim 1, wherein said information is arranged on a primary package of said medicaments or on a secondary package of said medicaments.

8. The system according to claim 1, wherein said device for obtaining medicament related information further comprises user communication elements capable of providing a user with information read by said reader.

9. The system according to claim 8, wherein said user communication elements comprise an audio interface.

10. The system according to claim 8, wherein said user communication elements comprise a video interface.

11. The system according to claim 8, wherein said user communication elements comprise transferring elements to external objects.

12. The system according to claim 11, wherein said transferring elements comprises data port for wired connection with external objects.

13. The system according to claim 11, wherein said transferring elements comprise wireless data communication elements.

14. The system according to claim 13, wherein said wireless data communication elements comprise near frequency communication technology.

15. The system according to claim 14, wherein said data communication elements comprise cellular radio communication technology.

16. The system according to claim 14, wherein said data communication elements comprise wireless local area networks.

17. A device for obtaining medicament related information to be used in a system according to claim 1.

* * * * *